US012582315B2

(12) United States Patent
Tamura et al.

(10) Patent No.: US 12,582,315 B2
(45) Date of Patent: Mar. 24, 2026

(54) ELECTROCARDIOGRAM ANALYSIS APPARATUS, ELECTROCARDIOGRAM ANALYZING METHOD, AND NON-TRANSITORY COMPUTER-READABLE STORAGE MEDIUM

(71) Applicant: CARDIO INTELLIGENCE INC., Tokyo (JP)

(72) Inventors: Yuichi Tamura, Tokyo (JP); Hirohisa Taniguchi, Tokyo (JP); Tomohiro Takata, Tokyo (JP); Tadahiro Taniguchi, Shiga (JP)

(73) Assignee: CARDIO INTELLIGENCE INC., Tokyo (JP)

( * ) Notice: Subject to any disclaimer, the term of this patent is extended or adjusted under 35 U.S.C. 154(b) by 295 days.

(21) Appl. No.: 17/811,860

(22) Filed: Jul. 11, 2022

(65) Prior Publication Data

US 2022/0346647 A1 Nov. 3, 2022

Related U.S. Application Data

(63) Continuation of application No. PCT/JP2021/008444, filed on Mar. 4, 2021.

(30) Foreign Application Priority Data

Apr. 8, 2020 (JP) ................................. 2020-069705

(51) Int. Cl.
  *A61B 5/00* (2006.01)
  *A61B 5/361* (2021.01)
(52) U.S. Cl.
  CPC ............ *A61B 5/0006* (2013.01); *A61B 5/361* (2021.01); *A61B 5/7267* (2013.01)

(58) Field of Classification Search
  CPC ..... A61B 5/0006; A61B 5/361; A61B 5/7267; A61B 5/363
  See application file for complete search history.

(56) References Cited

U.S. PATENT DOCUMENTS 10,959,660 B2 * 3/2021 Li ........................ A61B 5/7264
2016/0331247 A1 11/2016 Albert
(Continued)

FOREIGN PATENT DOCUMENTS

CA 3071699 A1 * 2/2019 ............. A61B 5/316
CN 110403600 A 11/2019
(Continued)

OTHER PUBLICATIONS

Translation of JP 2007195693 A (Year: 2007).*
(Continued)

*Primary Examiner* — Niketa Patel
*Assistant Examiner* — Attiya Sayyada Hussaini
(74) *Attorney, Agent, or Firm* — HAUPTMAN HAM, LLP

(57) ABSTRACT

An electrocardiogram analysis apparatus includes a machine learning part that has a machine learning model realized by machine learning that uses training electrocardiogram data of a patient with paroxysmal arrhythmia during a non-paroxysmal period during which no episode of paroxysmal arrhythmia occurs; an input processing part that inputs electrocardiogram data of a person to be analyzed, which is a subject of analysis, into the machine learning model; and an output control part that outputs, to an information terminal, abnormality information which is to be output from the machine learning model and is about whether the person to be analyzed has paroxysmal arrhythmia.

11 Claims, 4 Drawing Sheets

(56) References Cited

U.S. PATENT DOCUMENTS

| 2019/0104948 A1* | 4/2019 | Albert | G16H 40/63 |
| 2019/0328251 A1* | 10/2019 | Jin | A61B 5/02405 |
| 2020/0196886 A1 | 6/2020 | Perumalla et al. | |
| 2020/0352462 A1* | 11/2020 | Pedalty | A61B 5/363 |
| 2023/0360766 A1* | 11/2023 | Rosenberg | A63B 24/0075 |
| 2024/0099593 A1* | 3/2024 | Valys | G16H 50/70 |

FOREIGN PATENT DOCUMENTS

| JP | 2007195693 A | * | 8/2007 | |
| JP | 2018519122 A | | 7/2018 | |
| JP | 2019115618 A | | 7/2019 | |
| JP | 2019187966 A | | 10/2019 | |
| WO | WO-2019046294 A1 | * | 3/2019 | A61B 5/316 |

OTHER PUBLICATIONS

Jordan, Jeremy. "Neural networks: training with backpropagation." data science (2017) (Year: 2017).*

Elias Ebrahimzadeh et al., Prediction of paroxysmal Atrial Fibrillation: a machine learning based approach using combined feature vector and mixture of expert classification on HRV signal, Computer Methods and Programs in Biomedicine, Elsevier, Amsterdam, NL, vol. 165, Aug. 10, 2018, pp. 53-67, 15pp.

* cited by examiner

ELECTROCARDIOGRAM ANALYSIS APPARATUS, ELECTROCARDIOGRAM ANALYZING METHOD, AND NON-TRANSITORY COMPUTER-READABLE STORAGE MEDIUM

CROSS-REFERENCE TO RELATED APPLICATIONS

The present application is a continuation application of International Application number PCT/JP2021/8444, filed on Mar. 4, 2021, which claims priority under 35 U.S.C. § 119(a) to Japanese Patent Application No. 2020-69705, filed on Apr. 8, 2020. The contents of these applications are incorporated herein by reference in their entirety.

BACKGROUND OF THE INVENTION

The present disclosure relates to an electrocardiogram analysis apparatus, a method for analyzing an electrocardiogram, and a non-transitory computer-readable storage medium.

Conventionally, a Holter monitor that can be worn on the body of a patient to measure an electrocardiogram over a long period is known (see Japanese Unexamined Patent Application Publication No. 2007-195693, for example).

A waveform abnormality that can be evaluated with an electrocardiogram includes arrhythmia that occurs paroxysmally. In paroxysmal arrhythmia, episodes occur infrequently such as once a day to once every few months, for example. As paroxysmal arrhythmias, specifically, there are ventricular fibrillation and paroxysmal tachycardia such as paroxysmal atrial fibrillation, ventricular tachycardia, supraventricular tachycardia, atrial flutter, or the like. The electrocardiogram exhibits an electrocardiogram waveform in sinus rhythm when no episode is occurring. Therefore, even if an electrocardiogram of a subject person of electrocardiogram analysis is measured for a long period (e.g., 24 hours) with a Holter monitor, the electrocardiogram does not necessarily include a waveform of an episode. Therefore, there were cases where it was difficult to specify whether the subject person had paroxysmal arrhythmia.

BRIEF SUMMARY OF THE INVENTION

The present disclosure focuses on this point, and its object is to make it easier to specify whether or not a subject person of electrocardiogram analysis has paroxysmal arrhythmia.

An electrocardiogram analysis apparatus according to a first aspect of the present disclosure includes: a machine learning part that has a machine learning model realized by machine learning that uses training electrocardiogram data of a patient with paroxysmal arrhythmia during a non-paroxysmal period during which no episode of the paroxysmal arrhythmia occurs; an input processing part that inputs electrocardiogram data of a person to be analyzed, which is a subject of analysis, into the machine learning model; and an output control part that outputs, to an information terminal, abnormality information which is to be output from the machine learning model and is about whether the person to be analyzed has the paroxysmal arrhythmia.

A method for analyzing an electrocardiogram according to a second aspect of the present disclosure, executed by a computer, includes the steps of: acquiring a machine learning model that is realized by machine learning that uses training electrocardiogram data of a patient with paroxysmal arrhythmia during a non-paroxysmal period during which no episode of the paroxysmal arrhythmia occurs; inputting electrocardiogram data of a person to be analyzed, which is a subject of analysis, into the machine learning model; and outputting, to an information terminal, abnormality information which is to be output from the machine learning model and is about whether the person to be analyzed has the paroxysmal arrhythmia.

A non-transitory computer-readable storage medium according to a third aspect of the present disclosure stores a program that causes a computer to function as: a machine learning part that has a machine learning model realized by machine learning that uses training electrocardiogram data of a patient with paroxysmal arrhythmia during a non-paroxysmal period during which no episode of the paroxysmal arrhythmia occurs; an input processing part that inputs electrocardiogram data of a person to be analyzed, which is a subject of analysis, into the machine learning model; and an output control part that outputs, to an information terminal, abnormality information which is to be output from the machine learning model and is about whether the person to be analyzed has the paroxysmal arrhythmia.

DETAILED DESCRIPTION OF THE INVENTION

Hereinafter, the present disclosure will be described through exemplary embodiments, but the following exemplary embodiments do not limit the invention according to the claims, and not all of the combinations of features described in the exemplary embodiments are necessarily essential to the solution means of the invention.

[Outline of an Electrocardiogram (ECG) Analysis System S]

Figure 1:
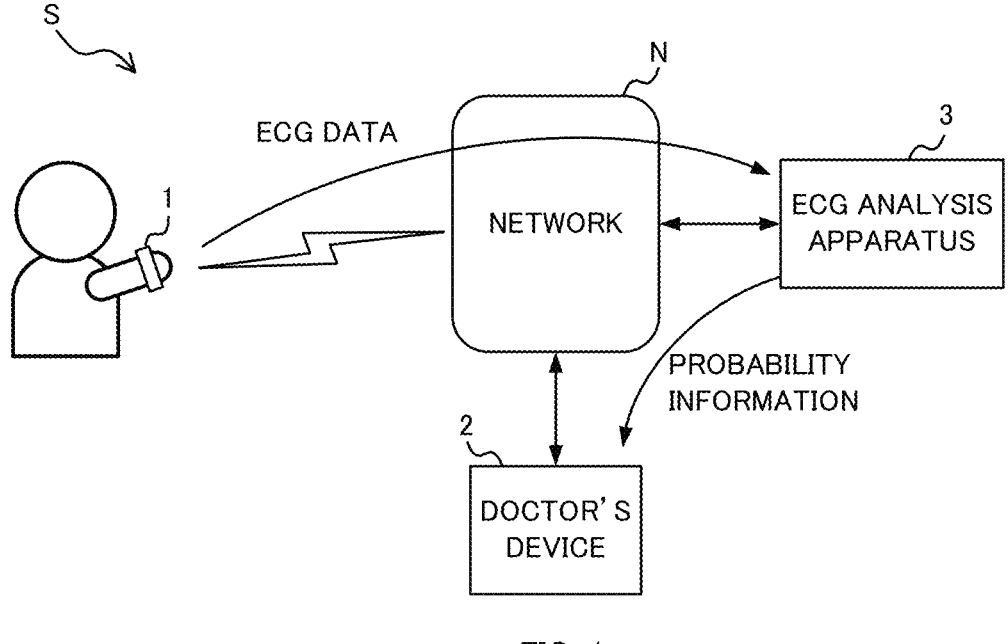
FIG. 1 illustrates an outline of an electrocardiogram analysis system.

FIG. 1 illustrates an outline of an electrocardiogram analysis system S according to the present embodiment. The electrocardiogram analysis system S includes an electrocardiograph 1, a doctor's device 2, and an electrocardiogram analysis apparatus 3. A plurality of electrocardiographs 1 and a plurality of doctor's devices 2 may be provided. The electrocardiogram analysis system S may include equipment such as other servers and terminals.

The electrocardiograph 1 is an electrocardiograph worn by a person, and is electrocardiogram measurement equipment that generates electrocardiogram data which indicates his/her electrocardiogram by measuring a potential while being worn on his/her wrist, palm, chest, or the like, for example. The electrocardiograph 1 is a Holter monitor (also referred to as a wearable electrocardiograph or a continuously mounted electrocardiograph), for example. The electrocardiograph 1 transmits the generated electrocardiogram data to the electrocardiogram analysis apparatus 3 via a network N including a wireless communication line. The electrocardiogram data generated by the electrocardiograph 1 may be sent to the electrocardiogram analysis apparatus 3 using a storage medium without passing through the network N, for example.

The doctor's device 2 is an information terminal used by a medical worker such as a doctor who examines a person, and includes a display (display device) and a computer, for example. The doctor's device 2 is associated in advance with a medical worker who uses the doctor's device 2 with an ID or the like given to the medical worker. The doctor's device 2 outputs abnormality information output by the electrocardiogram analysis apparatus 3 on the basis of the electrocardiogram data generated by the electrocardiograph 1. The doctor's device 2 may display the abnormality information on the display and may output voice indicating the abnormality information from a speaker.

The electrocardiogram analysis apparatus 3 is an apparatus that outputs abnormality information about whether a person to be analyzed has paroxysmal arrhythmia on the basis of the electrocardiogram data generated by the electrocardiograph 1, and is a server, for example. The abnormality information is (i) information representing a value, a level, or a score of the probability that the person to be analyzed has paroxysmal arrhythmia and (ii) whether there is paroxysmal arrhythmia or signs of paroxysmal arrhythmia in the person to be analyzed, for example. Further, the abnormality information may be information representing a value, a level, or a score of the probability that the person to be analyzed has no paroxysmal arrhythmia. Alternatively, the abnormality information may be information representing whether there is paroxysmal arrhythmia in the person to be analyzed. Further, the abnormality information may be information about an occurrence of other paroxysmal arrhythmias. Paroxysmal arrhythmia is at least one of ventricular fibrillation or paroxysmal tachycardia such as paroxysmal atrial fibrillation, ventricular tachycardia, supraventricular tachycardia, atrial flutter, or the like.

Figure 2:
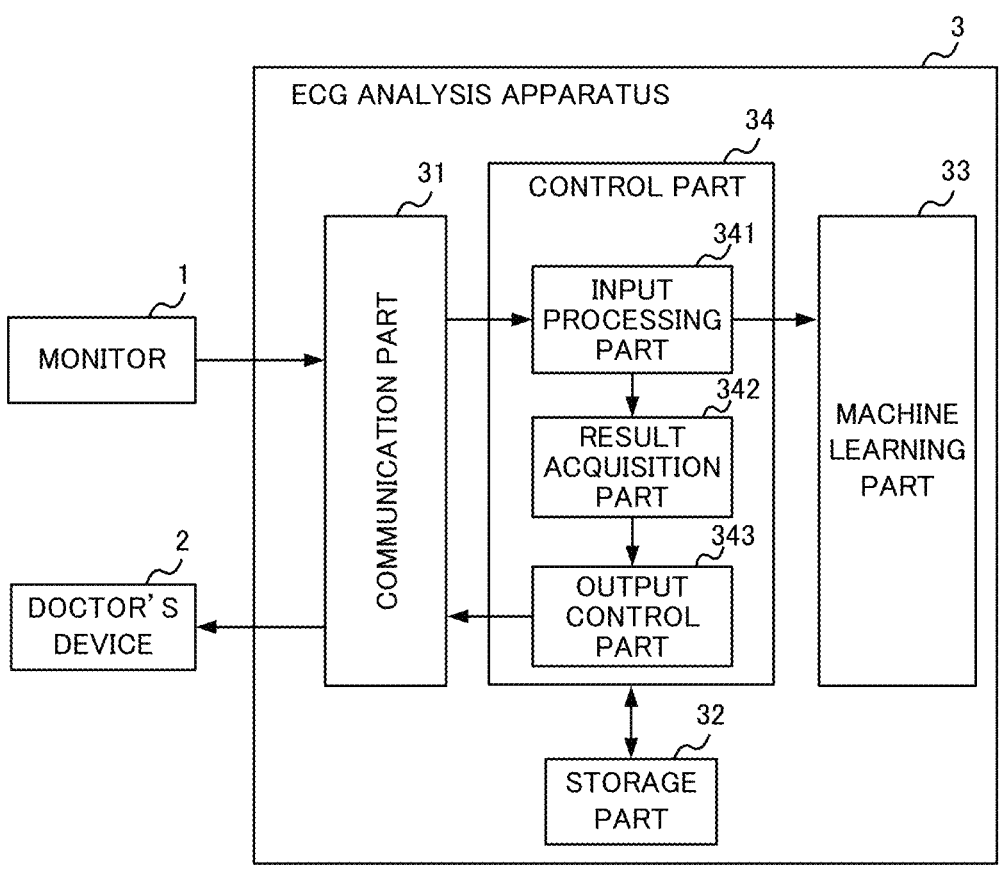
FIG. 2 is a block diagram of the electrocardiogram analysis system according to the embodiment.

FIG. 2 is a block diagram of the electrocardiogram analysis system S according to the present embodiment. Arrows indicate main data flows in FIG. 2, and there may be data flows not shown in FIG. 2. In FIG. 2, each block is not a hardware (device) unit but a functional unit. In FIG. 2, each block indicates a configuration of a function unit, not a configuration of a hardware (device) unit. Therefore, the blocks shown in FIG. 2 may be implemented in a single device or separately in a plurality of devices. The transfer of data between the blocks may be performed via any means, such as a data bus, a network, a portable storage medium, or the like.

The electrocardiogram analysis apparatus 3 includes a communication part 31, a storage part 32, a machine learning part 33, and a control part 34. The control part 34 includes an input processing part 341, a result acquisition part 342, and an output control part 343.

The communication part 31 has a communication controller for transmitting and receiving data between the electrocardiograph 1 and the doctor's device 2 via the network N. The communication part 31 notifies the control part 34 of the data received from the electrocardiograph 1 and the doctor's device 2 via the network N. The communication part 31 transmits the data output from the control part 34 to the doctor's device 2 via the network N.

The storage part 32 is a storage medium including a read only memory (ROM), a random access memory (RAM), a hard disk drive, and the like. The storage part 32 stores in advance a program executed by the control part 34. The storage part 32 may be provided outside the electrocardiogram analysis apparatus 3, and in such a case, the storage part may transmit and receive the data to and from the control part 34 via the network N.

By learning on the basis of electrocardiogram data for training (hereinafter, training electrocardiogram data), which is to be used as training data, the machine learning part 33 generates a machine learning model that outputs abnormality information about whether paroxysmal arrhythmia is included in electrocardiogram data that is input to the machine learning part 33 and holds the generated machine learning model. The machine learning model is a model generated by machine learning (i) normal electrocardiogram data (e.g., electrocardiogram data of a person who has no paroxysmal arrhythmia) and (ii) abnormal electrocardiogram data (e.g., electrocardiogram data of a person with paroxysmal arrhythmia) as training data. The machine learning part 33 may hold a machine learning model generated outside the electrocardiogram analysis apparatus 3.

An internal configuration of the machine learning model is any desired configuration, and it includes a convolutional neural network (CNN) or a recurrent neural network (RNN), for example. The machine learning part 33 includes a processor that executes various calculations using the CNN, and a memory that stores coefficients of the CNN, for example. The machine learning model of the machine learning part 33 outputs the abnormality information about whether the person to be analyzed has paroxysmal arrhythmia on the basis of the input electrocardiogram data. The machine learning part 33 may include only a memory for storing the machine learning model generated outside the electrocardiogram analysis apparatus 3. At least some of the functions of the machine learning part 33 may be built into the control part 34.

The control part 34 includes a processor such as a central processing unit (CPU) and functions as an input processing part 341, a result acquisition part 342, and an output control part 343 by executing the program stored in the storage part 32, for example. At least some of the functions of the control part 34 may be executed by an electric circuit. Further, at least some of the functions of the control part 34 may be executed by the control part 34 executing a program executed via a network.

The input processing part 341 inputs electrocardiogram data of a person to be analyzed, which is the subject of analysis, into the machine learning model of the machine learning part 33. The result acquisition part 342 acquires information output by the machine learning model of the machine learning part 33. The output control part 343 outputs, to the doctor's device 2, abnormality information which is to be output from the machine learning model of the machine learning part 33 and corresponds to whether the person to be analyzed has paroxysmal arrhythmia. Detailed processing executed by the input processing part 341, the result acquisition part 342, and the output control part 343 will be described later.

The electrocardiogram analysis system S according to the present embodiment is not limited to the specific configuration shown in FIG. 2. The electrocardiograph 1, the doctor's device 2, and the electrocardiogram analysis apparatus 3 may be configured by connecting two or more physically separated devices in a wired or wireless manner. The electrocardiogram analysis apparatus 3 may be formed by a single computer, may be formed by a plurality of computers cooperating with each other, or may be formed by a cloud which is a collection of computer resources. Two or more of the electrocardiograph 1, the doctor's device 2, and the electrocardiogram analysis apparatus 3 may be formed as one device.

[Description of an Electrocardiogram Analysis Method]

Figure 3:
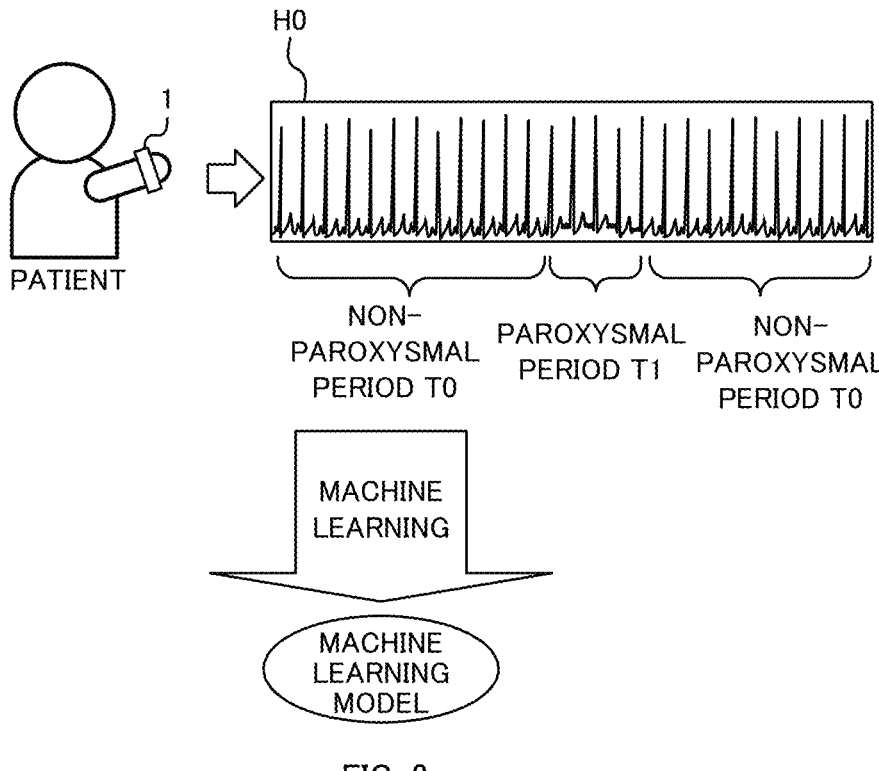
FIG. 3 is a schematic diagram illustrating a method in which the electrocardiogram analysis apparatus performs machine learning.

Hereinafter, an electrocardiogram analysis method executed by the electrocardiogram analysis system S according to the present embodiment will be described in detail. The electrocardiogram analysis apparatus 3 generates a machine learning model by machine learning in advance using the training electrocardiogram data. FIG. 3 is a schematic diagram illustrating a method in which the electrocardiogram analysis apparatus 3 performs machine learning. The electrocardiograph 1 measures an electrocardiogram of a patient. The patient is a person who has been diagnosed by a doctor as having paroxysmal arrhythmia (for example, at least one of ventricular fibrillation or paroxysmal tachycardia such as paroxysmal atrial fibrillation, ventricular tachycardia, supraventricular tachycardia, atrial flutter, or the like). The electrocardiograph 1 generates electrocardiogram data H0 indicating the measured electrocardiogram and transmits the electrocardiogram data H0 to the electrocardiogram analysis apparatus 3 via the network N.

In the electrocardiogram analysis apparatus 3, the input processing part 341 acquires the electrocardiogram data H0 transmitted by the electrocardiograph 1. In a patient who has paroxysmal arrhythmia, there are (i) a non-paroxysmal period T0 during which no episode of arrhythmia occurs and (ii) a paroxysmal period T1 during which an episode of arrhythmia occurs. The doctor can specify the paroxysmal period T1 by observing the electrocardiogram. The non-paroxysmal period T0 is a predetermined period of at least one of before or after the paroxysmal period T1, which is specified by the doctor as a period during which an episode of arrhythmia occurs and is a period which is not specified by the doctor as the period during which the episode of arrhythmia occurs (e.g., a period in which no abnormal condition due to paroxysmal arrhythmia occurs). The non-paroxysmal period T0 is preferably 7 days before or after the paroxysmal period T1, more preferably 24 hours before or after the paroxysmal period T1.

The input processing part 341 inputs, as training electrocardiogram data of a person who has paroxysmal arrhythmia, the non-paroxysmal period T0 portion within the electrocardiogram data H0 to the machine learning part 33. Further, the input processing part 341 inputs, as training electrocardiogram data of a person who has no paroxysmal arrhythmia, electrocardiogram data of a person who has been diagnosed by the doctor as not having paroxysmal arrhythmia to the machine learning part 33.

It is desirable that the input processing part 341 uses, as the training electrocardiogram data, electrocardiogram data of a predetermined period of time during which a person is at rest (e.g., during sleep). Further, it is desirable that the input processing part 341 uses, as the training electrocardiogram data, electrocardiogram data of a period in which the doctor has specified that symptoms different from paroxysmal arrhythmia to be analyzed have not occurred. By doing this, the electrocardiogram analysis system S can exclude data that may be noise and improve the accuracy of machine learning.

The machine learning part 33 generates a machine learning model that outputs abnormality information about whether the input electrocardiogram data is the electrocardiogram data of a person with paroxysmal arrhythmia, by performing known machine learning (e.g., the CNN or the RNN) using the input training electrocardiogram data. The machine learning part 33 may acquire a machine learning model generated with an external apparatus (server or the like) by the above-described machine learning method.

Figure 4:
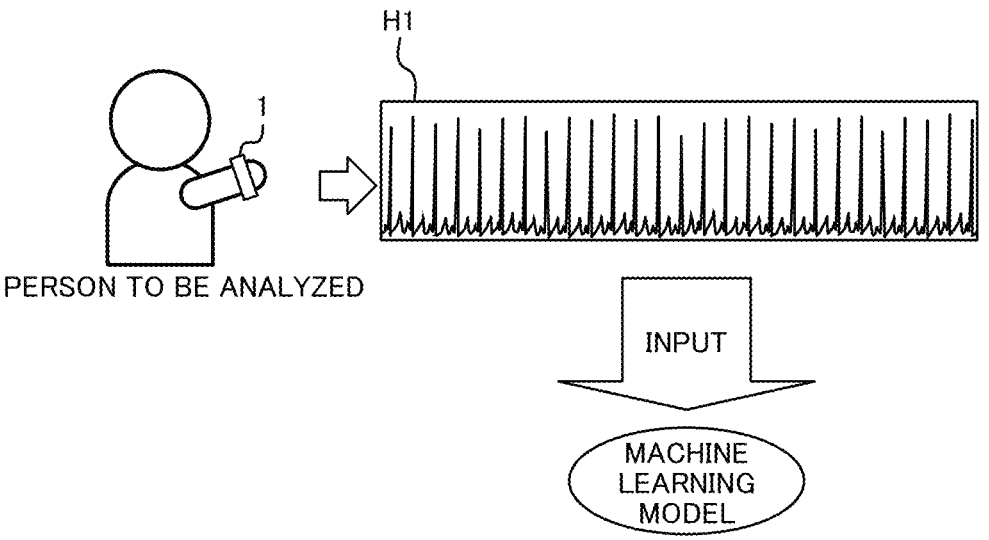
FIG. 4 is a schematic diagram illustrating a method in which the electrocardiogram analysis apparatus analyzes electrocardiogram data.

Next, the electrocardiogram analysis apparatus 3 analyzes the electrocardiogram data of the person to be analyzed, which is the subject of analysis, using the machine learning model of the machine learning part 33. FIG. 4 is a schematic diagram illustrating a method in which the electrocardiogram analysis apparatus 3 analyzes electrocardiogram data. The electrocardiograph 1 measures an electrocardiogram of the person to be analyzed. The electrocardiograph 1 generates electrocardiogram data H1 indicating the measured electrocardiogram, and transmits the electrocardiogram data H1 to the electrocardiogram analysis apparatus 3 via the network N.

In the electrocardiogram analysis apparatus 3, the input processing part 341 acquires the electrocardiogram data H1 transmitted by the electrocardiograph 1. It is desirable that the input processing part 341 sequentially acquires the electrocardiogram data H1 measured by the electrocardiograph 1 (e.g., the Holter monitor or a patch electrocardiograph) worn by the person to be analyzed living daily life. By doing this, the electrocardiogram analysis system S can promptly notify the medical worker of the information about whether or not the person to be analyzed has paroxysmal arrhythmia. Further, the input processing part 341 may acquire electrocardiogram data indicating the electrocardiogram of the person to be analyzed measured in advance in a hospital or the like, electrocardiogram data acquired from an electrocardiograph mounted on a steering wheel of a car, electrocardiogram data acquired from a 12-lead electrocardiograph, electrocardiogram data acquired from an electrocardiograph mounted on a smart watch, or the like.

The input processing part 341 inputs the acquired electrocardiogram data H1, as electrocardiogram data to be analyzed, to the machine learning model of the machine learning part 33. Here, it is desirable that the input processing part 341 inputs, to the machine learning model, electrocardiogram data to be analyzed that has been measured at the same sampling rate (for example, 1000 Hz) as the training electrocardiogram data. By doing this, the electrocardiogram analysis apparatus 3 can prevent an analysis result from being affected by a difference between sampling rates of electrocardiogram data. If the sampling rate of the training electrocardiogram data is different from the sampling rate of the electrocardiogram data to be analyzed, the input processing part 341 may perform a process of converting the sampling rate on the electrocardiogram data to be analyzed, and then input the processed data to the machine learning model.

When the electrocardiogram data is input, the machine learning model of the machine learning part 33 outputs the abnormality information about whether the input electrocardiogram data is electrocardiogram data of a person with paroxysmal arrhythmia. For example, the machine learning model outputs, as the abnormality information, abnormality information about whether a person (e.g., the person to be analyzed), who is a measurement source of the input electrocardiogram data, has paroxysmal arrhythmia. The machine learning model outputs, as the abnormal information, at least one of (i) the value of the probability that the person to be analyzed has paroxysmal arrhythmia, (ii) the level of the probability that the person to be analyzed has paroxysmal arrhythmia, (iii) the score of the probability that the person to be analyzed has paroxysmal arrhythmia, (iv)

whether there is paroxysmal arrhythmia in the person to be analyzed, or (v) whether there are signs of paroxysmal arrhythmia in the person to be analyzed.

The result acquisition part 342 acquires, as the analysis result, the abnormality information about whether the person to be analyzed has paroxysmal arrhythmia, which is output from the machine learning model of the machine learning part 33. The output control part 343 outputs the abnormality information acquired by the result acquisition part 342 to the doctor's device 2. The abnormal information is represented by the value, the level, or the score of the probability that the person to be analyzed has paroxysmal arrhythmia, for example. Further, the abnormality information may be information indicating the value, the level, or the score of the probability that the person to be analyzed has no paroxysmal arrhythmia. The level of the probability is represented by a letter or symbol such as H (high), L (low), ○, x, or the like associated with each range of probability values, for example. The score of the probability is expressed by, for example, a score obtained by converting the probability by a predetermined equation.

Further, the abnormality information may be information indicating whether there is paroxysmal arrhythmia or any sign of paroxysmal arrhythmia in the person to be analyzed. Whether there is arrhythmia or not is indicated by a character or a symbol that indicates a determination result of whether there is arrhythmia or any sign of arrhythmia by the machine learning model, for example. Also, the abnormality information may be output for the overall electrocardiogram data or may be output in association with each of a plurality of periods forming the electrocardiogram data. The abnormality information may be information on occurrence of other paroxysmal arrhythmias.

The doctor's device 2 may display the abnormality information on the display, and may output a voice indicating the abnormality information from the speaker. The doctor's device 2 may directly display the abnormality information, or may convert the abnormality information into other information ("Reexamination required," "Medication required," or the like if the probability is equal to or greater than a predetermined value) and then output the information.

Figure 5:
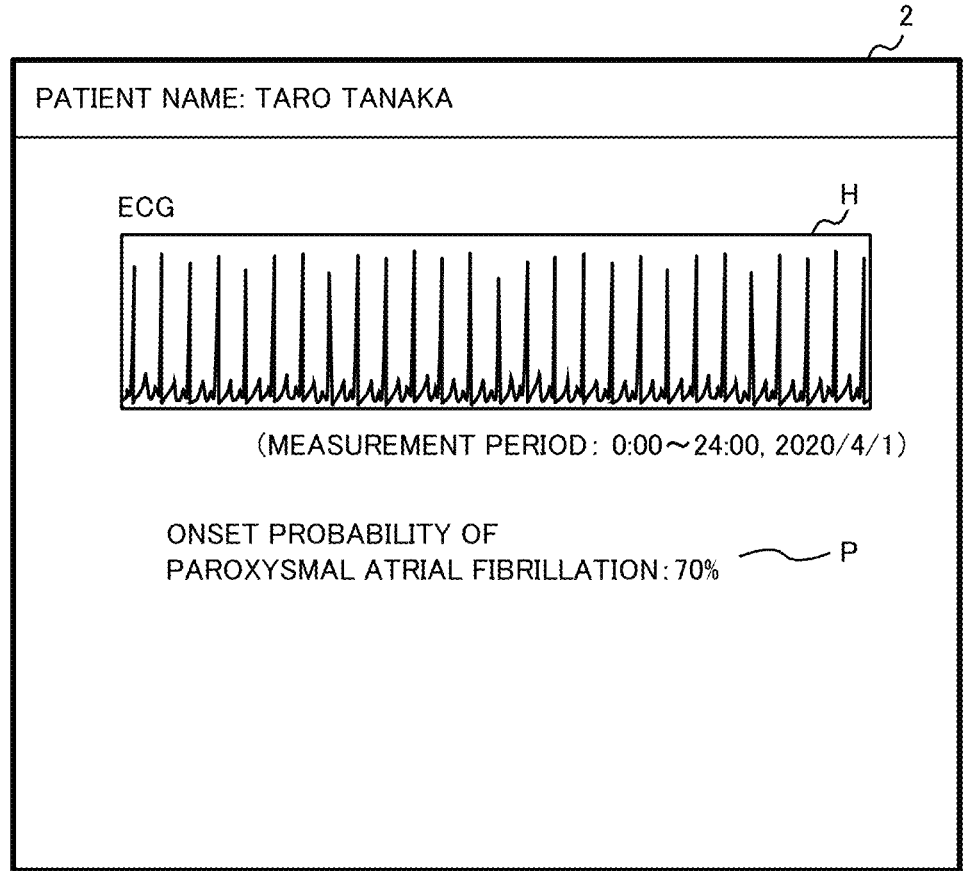
FIG. 5 is a schematic diagram of an analysis result screen displayed by a doctor's device.

FIG. 5 is a schematic diagram of an analysis result screen displayed by the doctor's device 2. The analysis result screen includes an electrocardiogram H and abnormality information P. The electrocardiogram H represents at least a part of the electrocardiogram data used for analysis. The abnormality information P represents the value or the level of the probability that the person to be analyzed has paroxysmal arrhythmia, which is output from the machine learning model, for example.

By analyzing the electrocardiogram by using the machine learning in this manner, the electrocardiogram analysis system S can detect signs of paroxysmal arrhythmia in a non-paroxysmal period that are difficult for a doctor to find with his/her eyes, and display the signs as the information about whether the person to be analyzed has paroxysmal arrhythmia. By referencing the electrocardiogram H and the abnormality information P displayed on the analysis result screen, the doctor can easily specify whether the person to be analyzed has paroxysmal arrhythmia, and can determine whether to do an additional examination or the like as needed.

The electrocardiogram analysis apparatus 3 may display changes in the probability in a plurality of different periods on the doctor's device 2. In this case, in the electrocardiogram analysis apparatus 3, the input processing part 341 inputs, as the electrocardiogram data to be analyzed, a plurality of pieces of electrocardiogram data indicating electrocardiograms of the person to be analyzed measured by the electrocardiograph 1 during the plurality of different periods (for example, a specific day of respective months) to the machine learning model of the machine learning part 33. The result acquisition part 342 acquires, in association with each of the plurality of different periods, the abnormality information about whether the person to be analyzed has paroxysmal arrhythmia output by the machine learning model.

The output control part 343 causes the doctor's device 2 to display the abnormality information about the changes in the probability of the plurality of different periods acquired by the result acquisition part 342. The abnormality information represents the changes in the probability by a graph that shows change over time or the level (difference, rate of change, or the like) of the change in the probability, for example. By referencing the changes in the probability displayed on the analysis result screen, the doctor can determine the risk of developing paroxysmal arrhythmia in the person to be analyzed.

The analysis result screen may include an area (e.g., a button or a selection box) for inputting a diagnosis on whether the person to be analyzed has paroxysmal arrhythmia diagnosed by a doctor. In this case, the doctor's device 2 transmits the input contents to the electrocardiogram analysis apparatus 3 as determination information on whether or not the person to be analyzed has paroxysmal arrhythmia.

The electrocardiogram analysis apparatus 3 receives the determination information transmitted by the doctor's device 2. By performing the above-described machine learning using the received determination information and the electrocardiogram data of the person to be analyzed, the machine learning part 33 regenerates the machine learning model that outputs the abnormality information about whether the input electrocardiogram data is the electrocardiogram data of the person with paroxysmal arrhythmia. By doing this, the electrocardiogram analysis system S can accept feedback on the diagnosis by the doctor and improve the accuracy of the abnormality information output by the machine learning model.

[Flowchart of the Electrocardiogram Analysis Method]

Figure 6:
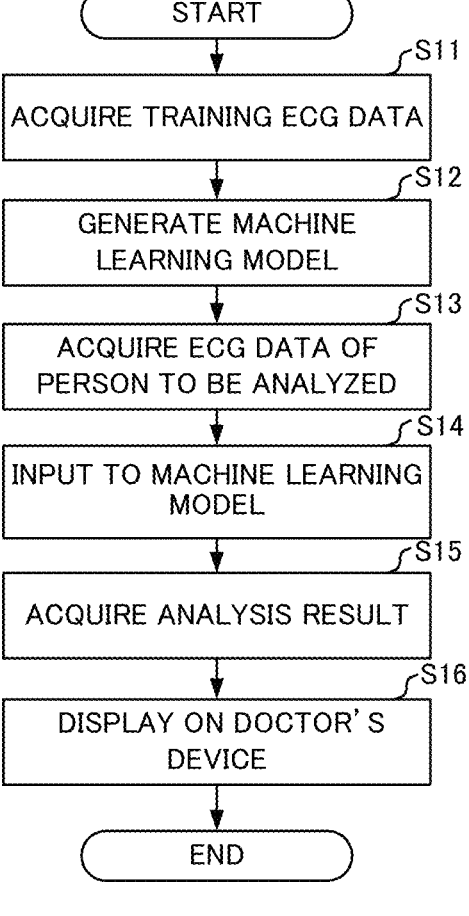
FIG. 6 is a flowchart of an electrocardiogram analysis method executed by the electrocardiogram analysis system according to the embodiment.

FIG. 6 is a flowchart of an electrocardiogram analysis method executed by the electrocardiogram analysis system S according to the present embodiment. The present embodiment includes the electrocardiogram analysis method illustrated in FIG. 6, a program for executing said electrocardiogram analysis method, and a non-transitory computer-readable storage medium storing the program. In the electrocardiogram analysis apparatus 3, the input processing part 341 acquires electrocardiogram data transmitted by the electrocardiograph 1 of a patient with paroxysmal arrhythmia (S11). The input processing part 341 inputs a non-paroxysmal period portion within the patient's electrocardiogram data to the machine learning part 33 as training electrocardiogram data of a person who has paroxysmal arrhythmia. Further, the input processing part 341 inputs electrocardiogram data of a person who has been diagnosed by a doctor as not having paroxysmal arrhythmia to the machine learning part 33 as training electrocardiogram data of a person who has no paroxysmal arrhythmia.

The machine learning part 33 generates a machine learning model that outputs abnormality information about whether the input electrocardiogram data is electrocardiogram data of a person with paroxysmal arrhythmia by machine learning using the input training electrocardiogram data (S12). When the machine learning part 33 uses the machine learning model generated outside the electrocardiogram analysis apparatus 3, steps S11 to S12 may be omitted.

The input processing part 341 acquires electrocardiogram data to be analyzed, which is transmitted by the electrocardiograph 1 of a person to be analyzed (S13). The input processing part 341 inputs the acquired electrocardiogram data as the electrocardiogram data to be analyzed into the machine learning model of the machine learning part 33 (S14). When the electrocardiogram data is input, the machine learning model of the machine learning part 33 outputs the abnormality information about whether the input electrocardiogram data is electrocardiogram data of a person with paroxysmal arrhythmia. The result acquisition part 342 acquires, as an analysis result, the abnormality information about whether the person to be analyzed has paroxysmal arrhythmia, which is output from the machine learning model of the machine learning part 33 (S15). The output control part 343 causes the doctor's device 2 to display the abnormality information about whether or not the result acquisition part 342 has acquired the abnormality information (S16).

Effect of the Embodiment

A patient's electrocardiogram measured within a limited period of time does not always include a waveform pertaining to an episode because episodes occur infrequently in paroxysmal arrhythmia. However, an electrocardiogram of a patient with paroxysmal arrhythmia shows signs of arrhythmia, which are difficult for a doctor to detect with his/her eyes even in the non-paroxysmal period during which no episode occurs. Therefore, the electrocardiogram analysis system S inputs the electrocardiogram data of the person to be analyzed into a machine learning model obtained by machine learning the electrocardiogram data of the patient with paroxysmal arrhythmia during his/her non-paroxysmal period, thereby outputting the abnormality information about whether the person to be analyzed has paroxysmal arrhythmia. By doing this, the electrocardiogram analysis system S can make it easier to specify whether the person to be analyzed has paroxysmal arrhythmia.

Modified Example

In the embodiment described above, the electrocardiogram analysis apparatus 3 is used for supporting a doctor to make a diagnosis, but the electrocardiogram analysis apparatus 3 may be used for other uses. For example, the electrocardiogram analysis apparatus 3 may be used in (i) a medical checkup result display system that displays whether there is a possibility of occurrence of paroxysmal arrhythmia in a person to be analyzed and whether a reexamination or a thorough checkup is required, on the basis of the abnormality information, (ii) an insurance examination support system in which the abnormality information is included in the eligibility criteria of an insurance plan of the person to be analyzed, and (iii) an insurance contract document apparatus in which the abnormality information is included in display items of insurance contract documents of the person to be analyzed. Therefore, the electrocardiogram analysis apparatus 3 can support screening an insurance application or the like on the basis of health conditions of the person to be analyzed.

Alternatively, the electrocardiogram analysis apparatus 3 may be used in a clinical trial participant selection system in which the abnormality information is included in display items of information concerning candidates for clinical trials. Therefore, the electrocardiogram analysis apparatus 3 can support making a determination such as excluding candidates who are likely to have paroxysmal arrhythmia from participants of a clinical trial on an evaluation of an electrocardiograph, for example.

Further, the electrocardiogram analysis apparatus 3 may be used as a drug administration determination support system or a drug administration contraindication determination support system which make use of the abnormality information. Therefore, the electrocardiogram analysis apparatus 3 can (i) support determination of the advisability of administering a drug or the like, which cannot be administered when there is arrhythmia, to a patient who is likely to have paroxysmal arrhythmia and (ii) use the abnormality information as a digital biomarker that stratifies patients who have paroxysmal disease, for example.

Further, the electrocardiogram analysis apparatus 3 may be used in a car driving control apparatus for safely stopping a vehicle when an episode of paroxysmal arrhythmia is detected while the vehicle is being driven, on the basis of the abnormality information. Alternatively, the electrocardiogram analysis apparatus 3 may be used in an alert system which recommends visiting a medical institution by displaying, on a smart device such as a smartphone, onset of paroxysmal arrhythmia on the basis of the abnormality information.

The present disclosure has been described above on the basis of the exemplary embodiments. The technical scope of the present disclosure is not limited to the scope explained in the above embodiments, and it is obvious to those skilled in the art that various changes and modifications within the scope of the invention may be made. An aspect to which such changes and modifications are added can be included in the technical scope of the present invention is obvious from the description of the claims.

The processor of the electrocardiogram analysis apparatus 3 performs each step (process) included in the electrocardiogram analysis method shown in FIG. 6. The processor of the electrocardiogram analysis apparatus 3 reads, from the storage part, a program for executing the electrocardiogram analysis method shown in FIG. 6 and executes the program to control each unit of the electrocardiogram analysis system S, thereby executing the electrocardiogram analysis method shown in FIG. 6. The steps included in the electrocardiogram analysis method shown in FIG. 6 may be partially omitted, the order among the steps may be changed, or a plurality of steps may be performed in parallel.

What is claimed is:

1. An electrocardiogram analysis apparatus, which supports determination of an advisability of doing an additional examination or administering a drug on a person to be analyzed, comprising:

a processor;

a memory;

a machine learning part that has a machine learning model, which is stored in the memory, realized by machine learning that uses first training electrocardiogram data of a patient who has been determined to have paroxysmal arrhythmia during a non-paroxysmal period during which a doctor determined by visual inspection in accordance with medical diagnostic criteria that no episode of the paroxysmal arrhythmia occurs, the non-paroxysmal period being a predetermined period of at least one of before or after a period during which the doctor determined in accordance with the medical diagnostic criteria that an episode of the paroxysmal arrhythmia occurs and second training electrocardiogram data of a person who has been determined not to have the paroxysmal arrhythmia so as to determine whether there is a sign of the paroxysmal arrhythmia in the non-paroxysmal period, the machine learning model outputting, when an electrocardiogram data of a person who has not been determined whether to have the paroxysmal arrhythmia is input, information regarding whether the input electrocardiogram data is an electrocardiogram data of a person having the paroxysmal arrhythmia;

an input processing part that inputs, by the processor, electrocardiogram data of the person to be analyzed who has not been determined whether to have the paroxysmal arrhythmia, which is a subject of analysis, into the machine learning model stored in the memory;

an output control part that displays, by the processor, on an information terminal, abnormality information and a portion of the non-paroxysmal period in electrocardiogram data associated with each other, where the abnormality information corresponds to information output from the machine learning model stored in the memory and is about whether the person to be analyzed has the paroxysmal arrhythmia, and the portion of the non-paroxysmal period in electrocardiogram data is inputted into the machine learning model in order to acquire the abnormality information; and a communication part configured to receive the electrocardiogram data from an electrocardiograph and transmit at least a part of the electrocardiogram data from the output control part to an external device.

2. The electrocardiogram analysis apparatus according to claim 1, wherein the machine learning part has the machine learning model stored in the memory that is realized by machine learning that uses the first training electrocardiogram data in the non-paroxysmal period which is a predetermined period of at least one of before or after a paroxysmal period, which is specified as a period during which an episode of the paroxysmal arrhythmia occurs.

3. The electrocardiogram analysis apparatus according to claim 1, wherein the machine learning part has the machine learning model stored in the memory that is realized by machine learning that uses the first training electrocardiogram data of the patient who has been determined to have at least one of paroxysmal atrial fibrillation, ventricular tachycardia, supraventricular tachycardia, atrial flutter, or ventricular fibrillation as the paroxysmal arrhythmia.

4. The electrocardiogram analysis apparatus according to claim 1, wherein the input processing part inputs the electrocardiogram data that has been measured at the same sampling rate as the first training electrocardiogram data to the machine learning model stored in the memory.

5. The electrocardiogram analysis apparatus according to claim 1, wherein the output control part outputs, to the information terminal, the abnormality information indicating a probability that the person to be analyzed has the paroxysmal arrhythmia.

6. The electrocardiogram analysis apparatus according to claim 5, wherein the input processing part inputs a plurality of pieces of the electrocardiogram data measured in a plurality of different periods to the machine learning model stored in the memory, and the output control part outputs, to the information terminal, the abnormality information about changes in the probability in the plurality of different periods.

7. The electrocardiogram analysis apparatus according to claim 1, wherein the input processing part inputs, to the machine learning model stored in the memory, the electrocardiogram data measured by an electrocardiograph worn by the person to be analyzed living daily life.

8. The electrocardiogram analysis apparatus according to claim 1, wherein the output control part outputs, to the information terminal, the abnormality information representing at least one of (i) a value, a level, or a score of the probability that the person to be analyzed has the paroxysmal arrhythmia, (ii) a value, a level, or a score of the probability that the person to be analyzed does not have the paroxysmal arrhythmia, (iii) whether there is the paroxysmal arrhythmia in the person to be analyzed, or (iv) whether there are signs of the paroxysmal arrhythmia in the person to be analyzed.

9. The electrocardiogram analysis apparatus according to claim 1, wherein the machine learning part receives, from the information terminal to which the abnormality information is output, determination information indicating whether or not the person to be analyzed has the paroxysmal arrhythmia, and regenerates the machine learning model by performing machine learning using the determination information and the electrocardiogram data.

10. A method for analyzing an electrocardiogram executed by a computer, which supports determination of an advisability of doing an additional examination or administering a drug on a person to be analyzed, comprising:

acquiring, by a processor, a machine learning model that is stored in the memory and is realized by machine learning that uses first training electrocardiogram data of a patient who has been determined to have paroxysmal arrhythmia during a non-paroxysmal period during which a doctor determined by visual inspection in accordance with medical diagnostic criteria that no episode of the paroxysmal arrhythmia occurs, the non-paroxysmal period being a predetermined period of at least one of before or after a period during which the doctor determined in accordance with the medical diagnostic criteria that an episode of the paroxysmal arrhythmia occurs and second training electrocardiogram data of a person who has been determined not to have the paroxysmal arrhythmia so as to determine whether there is a sign of the paroxysmal arrhythmia in the non-paroxysmal period, the machine learning model outputting, when an electrocardiogram data of a person who has not been determined whether to have the paroxysmal arrhythmia is input, information regarding whether the input electrocardiogram data is an electrocardiogram data of a person having the paroxysmal arrhythmia;

inputting, by the processor, electrocardiogram data of the person to be analyzed who has not been determined whether to have the paroxysmal arrhythmia, which is a subject of analysis, into the machine learning model stored in the memory;

displaying, by the processor, on an information terminal, abnormality information and a portion of the non-paroxysmal period in electrocardiogram data associated with each other, where the abnormality information corresponds to information output from the machine learning model stored in the memory and is about whether the person to be analyzed has the paroxysmal arrhythmia, and the portion of the non-paroxysmal period in electrocardiogram data is inputted into the machine learning model in order to acquire the abnormality information; and receiving, by a communication part, the electrocardiogram data from an electrocardiograph and transmitting at least a part of the electrocardiogram data from the output control part to an external device.

11. A system including an electrocardiograph and an electrocardiogram analysis apparatus, which supports determination of an advisability of doing an additional examination or administering a drug on a person to be analyzed, the electrocardiograph being configured to generate electrocardiogram data, and the electrocardiogram analysis apparatus comprising:
  a processor;
  a memory;
  a machine learning part that has a machine learning model, which is stored in the memory, realized by machine learning that uses first training electrocardiogram data of a patient who has been determined to have paroxysmal arrhythmia during a non-paroxysmal period during which a doctor determined by visual inspection in accordance with medical diagnostic criteria that no episode of the paroxysmal arrhythmia occurs, the non-paroxysmal period being a predetermined period of at least one of before or after a period during which the doctor determined in accordance with the medical diagnostic criteria that an episode of the paroxysmal arrhythmia occurs and second training electrocardiogram data of a person who has been determined not to have the paroxysmal arrhythmia so as to determine whether there is a sign of the paroxysmal arrhythmia in the non-paroxysmal period, the machine learning model outputting, when an electrocardiogram data of a person who has not been determined whether to have the paroxysmal arrhythmia is input, information regarding whether the input electrocardiogram data is an electrocardiogram data of a person having the paroxysmal arrhythmia;

an input processing part that inputs, by the processor, electrocardiogram data of the person to be analyzed who has not been determined whether to have the paroxysmal arrhythmia, which is a subject of analysis, into the machine learning model stored in the memory;

an output control part that displays, by the processor, on an information terminal, abnormality information and a portion of the non-paroxysmal period in electrocardiogram data associated with each other, where the abnormality information corresponds to information output from the machine learning model stored in the memory and is about whether the person to be analyzed has the paroxysmal arrhythmia, and the portion of the non-paroxysmal period in electrocardiogram data is inputted into the machine learning model in order to acquire the abnormality information; and a communication part configured to receive the electrocardiogram data from the electrocardiograph and transmit at least a part of the electrocardiogram data from the output control part to an external device.

* * * * *